United States Patent
Seo et al.

(10) Patent No.: US 6,630,156 B1
(45) Date of Patent: Oct. 7, 2003

(54) PROCESS FOR PREPARING BIODEGRADABLE MICROSPHERES CONTAINING PHYSIOLOGICALLY ACTIVE AGENTS

(75) Inventors: Min Hyo Seo, Taejon-si (KR); Jae Yong Lee, Daejon-si (KR); Jee Hyang Kim, Daejon-si (KR)

(73) Assignee: Samyang Corporation, Seoul (KR)

( * ) Notice: Subject to any disclaimer, the term of this patent is extended or adjusted under 35 U.S.C. 154(b) by 121 days.

(21) Appl. No.: 09/762,984

(22) PCT Filed: Jun. 15, 2000

(86) PCT No.: PCT/KR00/00636
§ 371 (c)(1),
(2), (4) Date: Apr. 23, 2001

(87) PCT Pub. No.: WO00/76483
PCT Pub. Date: Dec. 21, 2000

(30) Foreign Application Priority Data

Jun. 16, 1999 (KR) .......................... 1999-22471

(51) Int. Cl.$^7$ .............................. A61F 2/00; A61K 9/50; A61K 9/58; A61K 9/16
(52) U.S. Cl. ..................... 424/426; 424/499; 424/462; 424/493
(58) Field of Search ................................ 424/426, 499, 424/462, 493

(56) References Cited

U.S. PATENT DOCUMENTS 5,100,669 A  *  3/1992  Hyon et al. .................. 424/426

* cited by examiner

Primary Examiner—Jose' G. Dees
Assistant Examiner—R. DeWitty
(74) Attorney, Agent, or Firm—Thorpe North and Western, LLP

(57) ABSTRACT

The present invention relates to a process for preparing biodegradable microspheres containing physiologically active agents. Particularly, the present invention relates to the process comprised the following steps (1) to prepare a polymer solution containing physiologically active agents wherein a biodegradable polymer is dissolved in a water-soluble organic solvent and physiologically active agents are dissolved or suspended to it; (2) to form a O/O type emulsion by emulsifying the polymer solution into a water soluble alcohol which contains an emulsion stabilizer; and (3) to extract the organic solventS and alcohol by adding the emulsion into a neutral or an alkaline aqueous solution to educe the microspheres. The process of the present invention is effective for producing the microspheres having a uniform size which arm congenital to a living body and has an excellent inclusion efficiency. So, the microspheres prepared by the process of the present invention are used for a drug delivery system.

11 Claims, 1 Drawing Sheet

PROCESS FOR PREPARING BIODEGRADABLE MICROSPHERES CONTAINING PHYSIOLOGICALLY ACTIVE AGENTS

This application is a 371 of PCT/KR00/00636 filed Jun. 15, 2000.

FIELD OF THE INVENTION

The present invention relates to a process for preparing biodegradable microspheres containing a biologically active agent comprising: i) preparing a polymer solution containing the biologically active agents by dissolving a biodegradable polymer in a water soluble organic solvent followed by dissolving or suspending the physiologically active agents in the polymer solution; ii) forming an O/O emulsion by emulsifying the biological agents containing polymer solution into a water soluble alcohol which contains, an emulsion stabilizer; iii) extracting the water soluble organic solvent-and water soluble alcohol by adding the O/O emulsion into a neutral or alkaline aqueous solution, and precipitating and educing the microspheres containing the physiologically active agent from the solution. Particularly, the present invention relates to a method of producing sustained-release microspheres, having uniform size, which are compatible with a living body and have an excellent inclusion efficiency.

BACKGROUND

There is an increasing interest in developing a drug delivery system which is both safe and which provides for a high biological availability of the drug, i.e. to maximize pharmaceutical activity of known drugs as well as to minimize the side effects thereof. Due to their uniform release rate during the given time period and the non-toxic property of the degradation products, biodegradable polymers have been widely investigated as drug carriers. Biodegradable polymer drug carriers are especially useful for delivering drugs requiring continuous and sustained release with a single bolus administration, e.g. peptide or protein drugs, which should be administered daily because of quick loss of activity in the body.

Aliphatic polyesters, such as poly(lactic acid) (PLA), poly(glycolic acid) (PGA), copolymers of PLA and PGA (PLGA) or poly(carprolactone) (PCL), and polyanhydrides have been widely used for biodegradable polymers. They can be formulated as various shapes, such as films, strips, fibers, gels or microspheres, and the physiologically active agents are incorporated into the formulations and administered intramuscularly or subcutaneously. However, microspheres have been a particularly preferred formulation because the drug release rate can be easily controlled and the small microsphere particle sizes of 1~500 $\mu$m enables direct injection into the body by conventional methods. Preparation methods, however, to achieve uniform particle size of the microspheres and effective loading of drugs are still under investigation.

Microspheres have been prepared by various methods: solvent evaporation, phase separation, spray-drying, or solvent extraction at low temperature. However, improved methods for preparing microspheres having uniform particle size and effective drug loading are desirable. According to the solvent evaporation method, a hydrophobic polymer is dissolved in a water-immiscible organic solvent, such as dichloromethane, chloroform, or ethyl acetate, to give a polymer solution. Then, a physiologically active agent is dissolved or suspended in the polymer solution. The resulting solution is added into an aqueous solution of a surfactant to form an emulsion system, and microspheres are obtained by evaporating the solvent under vacuum or heating. Although this method is useful for very poorly water-soluble drugs it has very low loading efficiency for water-soluble drugs.

Ogawa et al. discloses a w/o/w double emulsion method for incorporating a water-soluble drug into microspheres (EP 190,833, U.S. Pat. No. 4,954,298, U.S. Pat. No. 4,652,441, and Korean patent 92-7831). According to their method, a biodegradable polymer is dissolved in a water-immiscible organic solvent to give a polymer solution, and a water-soluble physiologically active agent is emulsified into the polymer solution to give a w/o emulsion system. This emulsion is emulsified again into an aqueous solution of a surfactant to produce the w/o/w double emulsion system. The microspheres containing the water-soluble physiologically active agent are obtained by evaporating the solvent. This method requires gelatin be used to increase the viscosity of the w/o emulsion and the loading efficiency decreases remarkably because the particle size of the microsphere is less than 10 $\mu$m U.S. Pat. No. 4,675,189 discloses a phase separation method for preparing microcapsules. In this method an aqueous solution of a physiologically active agent is added into a polymer solution in an organic solvent to give a w/o emulsion. When the temperature, pH, or ionic strength of the w/o emulsion are changed or when a phase separating agent is added into the w/o emulsion, the polymer is precipitated around the water drops of the w/o emulsion.

Spray drying methods can also be employed for preparing microspheres, but this method has limitations due to the high temperatures required during processing. Spray drying methods require high temperatures for evaporating the solvent, and thus, they are not applicable for drugs that are unstable at high temperatures. In addition, a very low yield of microspheres also limits the use of this method.

Gombotz et al., U.S. Pat. No. 5,019,900, discloses a solvent extraction method wherein a physiologically active agent is dissolved or suspended into a polymer solution in an organic solvent, the resulting fluid is sprayed into a liquid of very low temperature, such as liquid argon, nitrogen or oxygen, and the organic solvent is extracted by cold ethanol from the frozen products. This method provides high loading efficiency of the drug, and is applicable for peptide or protein drugs that lose their biological activity easily at high temperatures. There are, however, several disadvantages of this method. For example, a special device is required for spraying the organic solvent; the porosity of the microspheres caused by the rapid freezing in the process results in rapid release of the drug from the microspheres; and some handling problems may arise from the use of liquid of very low temperature, such as liquid argon, nitrogen or oxygen.

In addition to the above methods, various other methods for preparing microspheres have also been used. These methods employ toxic organic solvents, e.g. dichloromethane or chloroform, for dissolving a biodegradable polymer such as polylactic acid. It is required that the residual organic solvents in the microspheres be restricted to within very low limits. The use of toxic organic solvents can also cause environmental problems.

Hyon et al., U.S. Pat. No. 5,100,669, discloses a method of preparing microspheres using acetic acid as the organic solvent. A biodegradable polymer and a physiologically active agent are dissolved in an aqueous solution of acetic acid, and the resulting solution is emulsified into water-immiscible oil (e.g. paraffin, mineral oil, and vegetable oil) or an organic solvent (e.g. toluene, xylene, and hexane) to give an O/O or w/o emulsion. The microspheres are obtained by evaporating the acetic acid. This method provides microspheres having a high drug-loading efficiency and with various particle sizes ranging from 0.01 to 300 μm. However, acetic acid should be evaporated at high temperature for longer than 12 hours due to its high boiling temperature (118° C.), and especially, the organic solvents (e.g. pentane, hexane, or heptane) which are used for separating the microspheres from the oil phase are toxic to the body and may cause environmental problems.

Therefore, a method of preparing efficiently, within a short time, a microsphere having good biocompatibility, high loading efficiency of a physiologically active agent, and uniform particle size, without use of a non-toxic organic solvent is greatly needed.

SUMMARY OF THE INVENTION

It is an object of this invention to provide a process which does not require use of a toxic organic solvent and the resulting microspheres have good biocompatibility, high loading efficiency of a physiologically active agent, and uniform particle size.

Further features of the present invention will appear hereinafter.

DETAILED DESCRIPTION OF PREFERRED EMBODIMENTS

Figure 1:
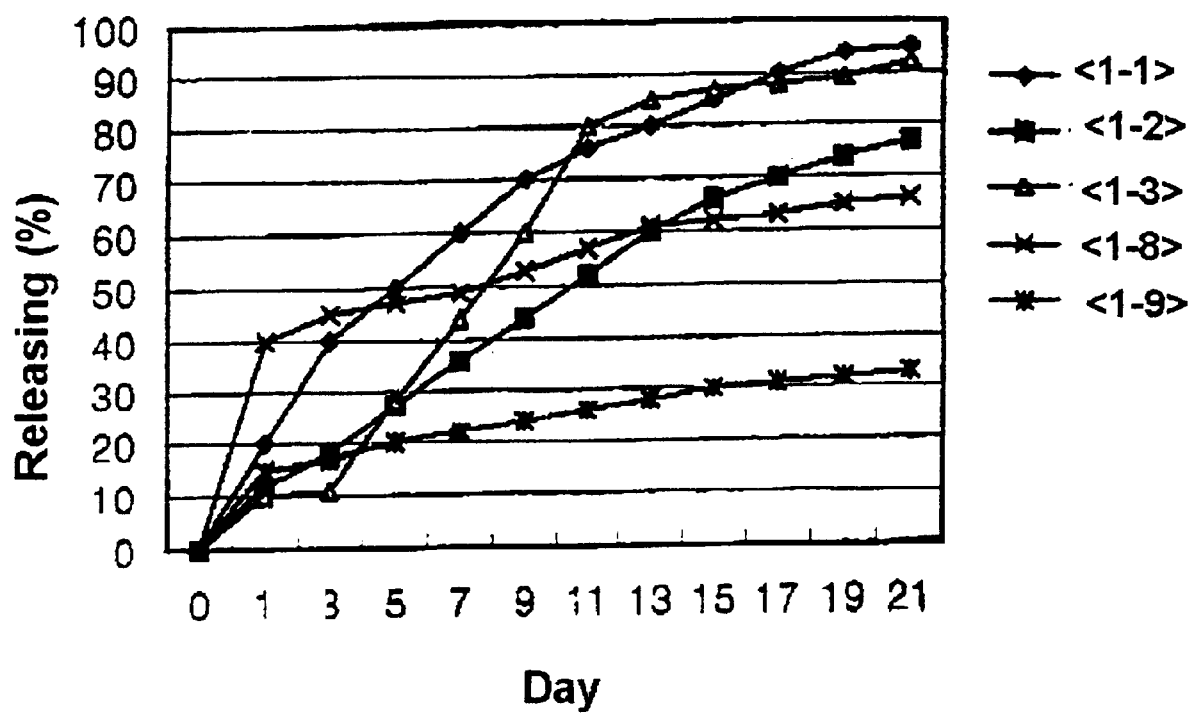
FIG. 1 is the release profile of a physiologically active agent from microspheres prepared by the present invention.

The process for preparing biodegradable microspheres containing a biologically active agent in the present invention comprises the following steps: i) preparing a polymer solution containing the biologically active agent by dissolving a biodegradable polymer in a water soluble organic solvent followed by dissolving or suspending the physiologically active agent in the polymer solution; ii) forming an O/O emulsion by emulsifying the biological agent containing polymer solution into a water soluble alcohol which contains an emulsion stabilizer; iii) extracting the water soluble organic solvent and water soluble alcohol by adding the O/O emulsion into a neutral or alkaline aqueous solution, and precipitating and educing the microspheres containing the physiologically active agent from the solution.

Hereinafter, the present invention is described in detail.

Preferably, the biodegradable polymer of the present invention is a member selected from the group consisting of an aliphatic polyester such as poly(lactic acid), a copolymer of lactic acid and glycolic acid, polycaprolactone, a copolymer of lactide and 1,4-dioxane-2-one, a copolymer of caprolactone and lactic acid, and a copolymer of caprolactone and glycolic acid, a polyorthoester, polyanhydride, polyphosphoamide, poly(amino acid), polyurethane, and di-, tri-, or multiblock copolymers of these hydrophobic polymers and hydrophilic poly(ethylene glycol). More preferably, it is a member selected from the group consisting of poly(lactic acid), copolymer of lactic acid and glycolic acid, polycaprolactone, a copolymer of lactide and 1,4-dioxane-2-one, and di-, tri-, or multiblock copolymers of these hydrophobic polymers and hydrophilic poly(ethylene glycol). The biodegradable polymers are biocompatible and their molecular weights are preferably within the range of 1,000~100,000 daltons, and more preferably within the range of 2,000~50,000 daltons.

The physiologically or biologically active agents of the present invention include peptide or protein drugs which require sustained physiological activity over an extend period of time, antiphlogistics, anti-cancer agents, antiviral agents, sex hormones, antibiotics, or anti-fungal agents. In detail, the physiologically active agents of the present invention include but are not limited to: peptide or protein drugs such as animal growth hormones including bovine growth hormone, porcine growth hormone, or sheep growth hormone, human growth hormone, granulocyte-colony stimulating factor (G-CSF), epithelial growth factor, bone morphogenic protein, erythropoietin, interferon, follicle stimulating hormone, leutenizing hormone, goserelin acetate, leuprorelin acetate, and leutenizing hormone-releasing hormone agonist including decapeptyl; antiphlogistics such as indomethacin, ibuprofen, ketoprofen, piroxicam, flubiprofen, and diclofenac; anti-cancer agents such as paclitaxel, doxorubicin, carboplatin, camptothecin, 5-fluorouracil, cisplatin, cytosine arabinose, and methotrexate; antiviral agents such as acyclovir and ribavirin; sex hormones such as testosterone, estrogen, progesterone, and estradiol; antibiotics such as tetracycline, minocycline, doxycycline, ofloxacin, levofloxacin, ciprofloxacin, clarithromycin, erythromycin, cefaclor, cefotaxime, imipenem, penicillin, gentamycin, streptomycin, and bancomycin; and anti-fungal agents such as ketoconazole, itraconazole, fluconazole, amphotericin-B, and griseofulvin.

The water-miscible organic solvents of the present invention are non-toxic to the body. Typical examples of organic solvents are members selected from the group consisting of acetic acid, lactic acid, formic acid, acetone, acetonitrile, dimethyl formamide, dimethyl acetamide, dimethyl sulfoxide, dioxane, and N-methyl pyrrolidone and mixtures thereof. Preferably, the water-miscible organic solvent is a member selected from the group consisting of acetic acid, lactic acid, N-methyl pyrrolidone, or a mixture thereof. The water-miscible organic solvent may be used alone or in a mixture with water.

The polymer solution containing a physiologically active agent of the present invention may be prepared by dissolving the biodegradable polymer and the physiologically active agent together into the organic solvent or by dissolving the biodegradable polymer into the organic solvent and then suspending the physiologically active agent into the polymer solution.

According to the present invention, an O/O emulsion is formed by emulsifying the above-prepared polymer solution containing a physiologically active agent into water-miscible alcohol. The water-miscible alcohol used as a suspending medium in the present invention is miscible with the above organic solvent as well as with water. Typical examples of the alcohol are members selected from the group consisting of methanol, ethanol, propanol, isopropanol, ethylene glycol, diethylene glycol, triethylene glycol, propylene glycol, glycerine, and mixtures thereof. Preferably, the water-miscible alcohol of the present invention is a member selected from the group consisting of methanol, ethanol, isopropanol, propylene glycol, and mixtures thereof.

The organic solvent and alcohol(suspending medium) used in the present invention are miscible with each other and with water. This is in contrast with the conventional methods of preparing a microsphere wherein the organic solvent used to dissolve a biodegradable polymer and the suspending medium, such as dichloromethane/water or acetic acid-water/oil are immiscible with each other. Water-miscible organic solvents and alcohols that are miscible with each other are preferably used, in the present invention, to prepare the microspheres due to the difference in solubility of the biodegradable polymer, such as poly(lactic acid). In other words, the polymer is freely soluble in an organic solvent but is insoluble in an alcohol.

When the polymer solution containing a physiologically active agent is directly emulsified into the water-miscible alcohol, a stable O/O emulsion may not be formed and the polymers precipitate in the medium since the water-miscible organic solvent dissolves rapidly in the water-miscible alcohol and, as a result, the solubility of the polymer decreases, rapidly and the polymers conglomerate together. In order to avoid this polymer precipitation, an emulsion stabilizer is preferably used in the present invention. When an emulsion stabilizer dissolves in the water-miscible alcohol (suspending medium), the viscosity of the medium increases and a stable O/O emulsion having no polymer precipitates can be formed.

The emulsion stabilizer of the present invention is preferably soluble in water and alcohol, is capable of increasing viscosity of the suspending medium(water-miscible alcohol) when dissolved in the medium, is non-toxic to the body and causes no environmental problems. Typical examples of emulsion stabilizers are: water-soluble synthetic polymers such as polyvinylpyrrolidone, poly(ethylene glycol), and poloxamer; cellulose derivatives such as hydroxypropyl cellulose and hydroxypropylmethyl cellulose, and preferably, polyvinylpyrrolidone and hydroxypropyl cellulose. The content of emulsion stabilizer in the water-miscible alcohol is preferably within the range of 0.1~50% (w/v), and more preferably within the range of 0.2~20%(w/v). The content of emulsion stabilizer can varied according to the-viscosity of the water-miscible alcohol needed. Non-ionic surfactants such as polyoxyethylenesorbitan esters or sorbitan esters, which are generally used as emulsion stabilizers, can't provide the desirable effects in the solvent system of the present invention.

According to the present invention, the water-miscible alcohol, wherein the emulsion stabilizer is dissolved, is stirred at a temperature of 10~80° C., preferably 20~60° C., at a speed of 200~20,000 rpm. The polymer solution containing a physiologically active agent is then slowly added to the water-miscible alcohol wherein the emulsion stabilizer is dissolved, and the mixture is stirred for 5~60 minutes to give a stable O/O emulsion. This emulsion is then added to a neutral or alkaline aqueous solution of pH 6~12 at a temperature of 0~30° C. to extract the organic solvent and alcohol, and to precipitate the microspheres of the present invention from the solution. The resulting microspheres are then filtered and freeze-dried for use.

The neutral or alkaline aqueous solution is preferably a common buffer solution of pH 6~10, and an alkaline aqueous solution is preferred when an organic acid, such as acetic acid, is used as the organic solvent.

The diameter of the microspheres prepared by the method of the present invention is preferably within the range from 0.01 to 300 um, and more preferably within the range from 0.1 to 100 um. Thus the microspheres prepared by the method of the present invention preferably contain a physiologically active agent up to 40 wt %, and more preferably within the range of 5~30 wt %. The particle size(diameter of the microspheres) can be controlled by adjusting the stirring speed during processing, the viscosity of the water-miscible alcohol, the viscosity of the polymer solution containing the physiologically active agent, and the volume ratio of the polymer solution containing a physiologically active agent to the water-miscible alcohol.

The microspheres prepared by the method of the present invention can be used as a drug delivery carrier capable of localizing and providing for the sustained release of drugs to a specific disease site after being administration by subcutaneous, intramuscular, or intravenous injection to an animal or a human body.

The microspheres prepared by the method of the present invention can also be used as a drug delivery carrier that, when injected directly into the disease site, releases a drug with a sustained rate and then degrades into small molecules that can be eliminated from the body.

The following examples will enable those skilled in the art to more clearly understand how to practice the present invention. It is to be understood that while the invention has been described in conjunction with the preferred specific embodiments thereof, that which follows is intended to illustrate and not limit the scope of the invention. Other aspects of the invention will be apparent to those skilled in the art to which the invention pertains.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Preparation of Microspheres Containing a Physiologically Active Agent

Example 1-1

A tetracycline containing polymer solution was formed by dissolving 0.8 g of poly(d,l-lactic acid) (molecular weight of 18,000 Daltons) and 0.2 g of tetracycline in 2 mL of acetic acid. The solution was slowly added to a 40 mL of an ethanol solution containing hydroxypropyl cellulose(5 w/v %), as an emulsion stabilizer, at 45° C. while stirring at 1,000 rpm. After 10 minutes of stirring, an O/O emulsion was formed and was added into 100 mL of 0.2M phosphate buffer solution(pH 8.5) thereby precipitating tetracycline containing polymeric microspheres. The micropheres were filtered and washed with distilled water.

Yield: 92%, Average particle size: 25 um, Drug loading efficiency: 95%.

Example 1-2

An ofloxicin containing polymer solution was formed by dissolving 0.8 g of poly(d,l-lactic acid) (molecular weight of 18,000 Daltons) and 0.2 g of ofloxacin in 2 mL of acetic acid. The solution was slowly added to. 40 mL of a methanol solution containing hydroxypropyl cellulose(5 w/v %), as an emulsion stabilizer, at 45° C. while stirring. The microspheres were prepared by the same method as in Example 1-1.

Yield: 96%, Average particle size: 40 um, Drug loading efficiency: 99%.

Example 1-3

A goserelin acetate containing polymer solutions was formed by dissolving 0.9 g, of a copolymer of d,l-lactic acid and glycolic acid (molecular weight of 12,000 Daltons, d,l-lactic acid/glycolic acid(wt/wt)=75/25) and 0.1 g of goserelin acetate in 1.5 mL of acetic acid. The solution was slowly added to 30 mL of an ethanol solution containing polyvinylpyrrolidone (2.5 w/v %), as an emulsion stabilizer, at 40° C. while stirring. The microspheres were prepared by the same method as in Example 1-1.

Yield: 90%, Average particle size: 20 um, Drug loading efficiency: 94%.

Example 1-4

A goserelin acetate polymer solution was prepared by dissolving 0.9 g of a copolymer of d,l-lactic acid and glycolic acid (molecular weight of 12,000 Daltons, d,l-lactic acid/glycolic acid(wt/wt)=75/25) and 0.1 g of goserelin acetate in 1.5 mL of acetic acid. The solution was slowly added to 30 mL of an ethylene glycol solution containing polyvinylpyrrolidone (2 w/v %), as an emulsion stabilizer, at 40° C. while stirring. The microspheres were prepared by the same method as in Example 1-1.

Yield: 97%, Average particle size: 44 um, Drug loading efficiency: 98%.

Example 1-5

A leuprorelin acetate polymer solution was prepared by dissolving 0.9 g of poly(d,l-lactic acid) (molecular weight of 18,000 Daltons) and 0.1 g of leuprorelin acetate in 1.5 mL of acetic acid. The solution was slowly added to 30 mL of a diethylene glycol solution containing polyvinylpyrrolidone(1.5 w/v %), as an emulsion stabilizer, at 45° C. while stirring. The microspheres were prepared by the same method as in Example 1-1.

Yield: 89%, Average particle size: 80 um, Drug loading efficiency: 98%.

Example 1-6

A leuprorelin acetate polymer solution was prepared by dissolving 0.9 g of poly(d,l-lactic acid) (molecular weight of 18,000 Daltons) and 0.1 g of leuprorelin acetate in 1.5 mL of acetic acid. The solution was slowly added to 30 mL of an isopropanol solution containing hydroxypropyl cellulose (5 w/v %), as an emulsion stabilizer, at 45° C. while stirring. The microspheres were prepared by the same method as in Example 1-1.

Yield: 92%, Average particle size: 22 um, Drug loading efficiency: 96%.

Example 1-7

An ofloxacin polymer solution was prepared by dissolving 0.9 g of poly(d,l-lactic acid) (molecular weight of 4,000 Daltons) and 0.1 g of ofloxacin in 2 mL of aqueous acetic acid solution(90%). The solution was slowly added to 40 mL of a triethylene glycol solution containing polyvinylpyrrolidone (0.5 w/v %), as an emulsion stabilizer, at 45° C. while stirring. The microspheres were prepared by the same method as in Example 1-1.

Yield: 96%, Average particle size: 55 um, Drug loading efficiency: 99%.

Example 1-8

A human growth hormone polymer solution was prepared by dissolving 0.85 g of poly(d,l-lactic acid) (molecular weight of 18,000 Daltons) and 0.15 g of human growth hormone in 2 mL of aqueous acetic acid solution(80%). The solution was slowly added to 40 mL of an ethanol solution containing polyvinylpyrrolidone (5 w/v %), as an emulsion stabilizer, at 40° C. while stirring. The microspheres were prepared by the same method as in Example 1-1.

Yield: 90%, Average particle size: 42 um, Drug loading efficiency: 94%.

Example 1-9

A porcine growth hormone polymer solution was prepared by dissolving 0.85 g of poly(d,l-lactic acid) (molecular weight of 18,000 Daltons) and 0.15 g of porcine growth hormone in 2 mL of aqueous acetic acid solution(80%). The solution was slowly added to 40 mL of an ethanol solution containing polyvinylpyrrolidone (5 w/v %), as an emulsion stabilizer, at 40° C. while stirring. The microspheres were prepared by the same method as in Example 1-1.

Yield: 93%, Average particle size: 40 um, Drug loading efficiency: 98%.

Example 1-10

A granulocyte-colony stimulating factor (G-CSF) polymer solution was prepared by dissolving 0.09 g of poly(d,l-lactic acid) (molecular weight of 4,000 Daltons) and 0.01 g of granulocyte-colony stimulating factor(G-CSF) in 0.2 mL of aqueous acetic acid solution(80%). The solution was slowly added to 2 mL of an ethanol solution containing polyvinylpyrrolidone (5 w/v %), as an emulsion stabilizer, at 40° C. while stirring. The microspheres were prepared by the same method as in Example 1-1.

Yield: 96%, Average particle size: 47 um, Drug loading efficiency: 96%.

Example 1-11

A porcine growth hormone polymer solution was prepared by dissolving 0.85 g of copolymer of d,l-lactide and 1,4-dioxane-2-on (molecular weight of 10,000 Daltons, d,l-lactide/1,4-dioxane-2-on(wt/wt)=50/50) and 0.15 g of porcine growth hormone in 2 mL of aqueous acetic acid solution(80%). The solution was slowly added to 30 mL of a methanol solution containing polyvinylpyrrolidone (5 w/v %), as an emulsion stabilizer, at 40° C. while stirring. The microspheres were prepared by the same method as in Example 1-1.

Yield: 92%, Average particle size: 40 um, Drug loading efficiency: 94%.

Example 1-12

A paclitaxel containing polymer solution was prepared by dissolving 0.45 g of poly(d,l-lactic acid) (molecular weight of 18,000 Daltons) and 0.05 g of paclitaxel in 0.5 mL of acetone. The solution was slowly added to 20 mL of a diethylene glycol solution containing polyvinylpyrrolidone (1 w/v %), as an emulsion stabilizer, at 60° C. while stirring. The O/O emulsion prepared by the same method of Example 1-1 was added to 40 mL of 0.01M phosphate buffer solution (pH7.4). The microspheres were prepared by the same method as in Example 1-1.

Yield: 95%, Average particle size: 55 um, Drug loading efficiency: 98%.

Example 1-13

A paclitaxel containing polymer solution was prepared by dissolving 0.45 g of a block copolymer of poly(d,l-lactic acid) (molecular weight of 5,000 Daltons) and monomethoxy poly(ethylene glycol) (molecular weight of 2,000 Daltons) and 0.05 g of paclitaxel in 0.5 mL of acetone. The solution was slowly added to 20 mL of a diethylene glycol solution containing polyvinylpyrrolidone (1 w/v %), as an emulsion stabilizer, at 50° C. while stirring at 12,000 rpm. The microspheres(nanospheres) were prepared by the same method as in Example 1-12.

Yield: 87%, Average particle size: 0.2 um, Drug loading efficiency: 94%).

Comparative Example 1

A tetracycline containing polymer solution was prepared by dissolving 0.8 g of poly(d,l-lactic acid) (molecular weight of 18,000 Daltons) and 0.2 g of tetracycline in 2 mL of acetic acid. The solution was slowly added to 40 mL of an ethanol containing no emulsion stabilizer at 45° C. while stirring. The mixture was processed by the same procedure as in Example 1-1, but polymer conglomerates were obtained instead of the desired microspheres. This illustrates that addition of an emulsion stabilizer at the step of forming the O/O emulsion is important to form the desired microsphere.

Comparative Example 2

A tetracycline containing polymer solution was prepared by dissolving 0.8 g of poly(d,l-lactic acid) (molecular weight of 18,000 Daltons) and 0.2 g of tetracycline in 2 mL of acetic acid. The solution was slowly added to 40 mL of an ethanol solution containing Tween 80(0.2 w/v %) at 45° C. while stirring. The mixture was processed by the same procedure as in Example 1-1, but polymer conglomerates were obtained instead of the desired microspheres. This indicates that nonionic surfactants such as Tween 80, which is not soluble in water and alcohol, can't provide the desired effect of the present invention.

Experimental Example 1

Release of a Physiologically Active Agent From the Microspheres

A 100 mg sample of each of the microspheres prepared in Examples 1-1, 1-2, 1-3, 1-8, and 1-9 was added to 2 mL of phosphate buffer solution (10 mM, pH 7.4) and stirred at 37° C. at 50 rpm. At given time intervals, each sample solution was centrifuged and the amount of physiologically active agent released from the microspheres into the buffer medium was assayed. The same amount of fresh buffer solution was added, and the above procedure was repeated to determine the released amount of the physiologically active agent. The release profile of the physiologically active agent from the microspheres prepared in Examples 1-1, 1-2, 1-3, 1-8, and 1-9 is shown in FIG. 1. As shown in FIG. 1, the microspheres prepared by the method of the present invention can be used as a drug delivery carrier having a sustained release profile.

INDUSTRIAL APPLICABILITY

The present invention provides a process for preparing biodegradable microspheres containing a biologically active agent comprising: i) preparing a polymer solution containing the biologically active agents by dissolving a biodegradable polymer in a water soluble organic solvent followed by dissolving or suspending the physiologically active agents in the polymer solution; ii) forming an O/O emulsion by emulsifying the biological agents containing polymer solution into a water soluble alcohol which contains an emulsion stabilizer; iii) extracting the water soluble organic solvent and water soluble alcohol by adding the O/O emulsion into a neutral or alkaline aqueous solution, and precipitating and educing the microspheres containing the physiologically active agent from the solution.

The resulting biologically active agent containing microspheres are compatible with a living body and have excellent inclusion efficiency and are particularly useful for sustained release drug delivery systems. Particularly, the present invention relates to a method of producing sustained-release microspheres, having uniform size, which are compatible with a living body and have an excellent inclusion efficiency.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A method for preparing a biodegradable microsphere containing a physiologically active agent, comprising the steps of:
   1) dissolving a biodegradable polymer in a water-miscible organic solvent to give a polymer solution, and dissolving or suspending said physiologically active agent in the polymer solution to give a polymer solution containing the physiologically active agent;
   2) emulsifying the polymer solution containing the physiologically active agent into a water-miscible alcohol containing an emulsion stabilizer to provide an O/O emulsion; and
   3) adding the O/O emulsion to a neutral or alkaline aqueous solution, and precipitating biodegradable polymeric microspheres containing the physiologically active agent from the aqueous solution.

2. The method of claim 1, wherein the biodegradable polymer is a member selected from the group consisting of poly(lactic acid), a copolymer of lactic acid and glycolic acid, polycaprolactone, a copolymer of lactide and 1,4-dioxane-2-on, a copolymer of caprolactone and lactic acid, a copolymer of caprolactone and glycolic acid, polyorthoester, polyanhydride, polyphosphoamide, poly (amino acid), polyurethane, and di-, tri-, or multiblock copolymers of these polymers and poly(ethylene glycol).

3. The method of claim 1, wherein the physiologically active agent is a member selected from the group consisting of peptide or protein drugs, antiphlogistics, anti-cancer agents, antiviral agents, sex hormones, antibiotics, antifungal agents, and a mixture thereof.

4. The method of claim 1, wherein the water-miscible organic solvent is a member selected from the group consisting of acetic acid, lactic acid, formic acid, acetone, acetonitrile, dimethyl formamide, dimethyl acetamide, dimethyl sulfoxide, dioxane, N-methyl pyrrolidone, and a mixture thereof.

5. The method of claim 1, wherein the water-miscible alcohol is a member selected from the group consisting of methanol, ethanol, propanol, isopropanol, ethylene glycol, diethylene glycol, triethylene glycol, propylene glycol, glycerine, and a mixture thereof.

6. The method of claim 1, wherein the emulsion stabilizer is a member selected from the group consisting of water-soluble synthetic polymers and cellulose derivatives.

7. The method of claim 1, wherein the emulsion stabilizer is a member selected from the group consisting of polyvinylpyrrolidone, poly(ethylene glycol), poloxamer, hydroxypropyl cellulose, and hydroxypropylmethyl cellulose and a mixture thereof.

8. The method of claim 1, wherein the concentration of the emulsion stabilizer in the water-miscible alcohol is within the range from 0.1 to 50 w/v %.

9. The method of claim 1, wherein the step 2) further comprising of adding the polymer solution containing a physiologically active agent slowly into the water-miscible alcohol containing the emulsion stabilizer at a temperature of 10~80° C. while stirring at a speed of 20~20,000 rpm for 5~60 minutes to give a stable O/O emulsion.

10. The method of claim 1, wherein the neutral or alkaline aqueous solution has pH between 6 to 12.

11. The method of claim 10, wherein the neutral or alkaline aqueous solution is a buffer solution of pH between 6 to 10.

* * * * *